United States Patent
Szabo

(10) Patent No.: US 12,357,373 B2
(45) Date of Patent: Jul. 15, 2025

(54) ROTATION MECHANISM FOR SURGICAL INSTRUMENTS

(71) Applicant: Conmed Corporation, Utica, NY (US)

(72) Inventor: Aaron Szabo, Swanton, OH (US)

(73) Assignee: Conmed Corporation, Utica, NY (US)

( * ) Notice: Subject to any disclaimer, the term of this patent is extended or adjusted under 35 U.S.C. 154(b) by 706 days.

(21) Appl. No.: 17/068,940

(22) Filed: Oct. 13, 2020

(65) Prior Publication Data

US 2021/0106377 A1 Apr. 15, 2021

Related U.S. Application Data

(60) Provisional application No. 62/914,597, filed on Oct. 14, 2019.

(51) Int. Cl.
*A61B 18/14* (2006.01)
*A61B 17/00* (2006.01)

(52) U.S. Cl.
CPC ...... *A61B 18/1445* (2013.01); *A61B 2017/00367* (2013.01)

(58) Field of Classification Search
CPC .............. A61B 2017/00367; A61B 18/1445
See application file for complete search history.

(56) References Cited

U.S. PATENT DOCUMENTS

| | | | | |
|---|---|---|---|---|
| 2011/0040308 A1* | 2/2011 | Cabrera | ............ | A61B 17/0491 606/144 |
| 2012/0184988 A1* | 7/2012 | Twomey | ............ | A61B 17/2812 606/205 |
| 2012/0310243 A1* | 12/2012 | Stratton | ............... | A61F 2/4644 606/79 |
| 2013/0296922 A1* | 11/2013 | Allen, IV | ........... | A61B 18/1445 606/205 |
| 2016/0100882 A1* | 4/2016 | Boudreaux | ........ | A61B 18/1445 606/52 |

* cited by examiner

*Primary Examiner* — Linda C Dvorak
*Assistant Examiner* — Ryan T Clark
(74) *Attorney, Agent, or Firm* — Bond, Schoeneck & King, PLLC; David L. Nocilly

(57) ABSTRACT

An electrosurgical instrument having a knob with an internal gear, a shaft extending from the body with an external gear that is coupled to the internal gear, and a pair of jaws mounted to the shaft. The internal gear and the external gear have a gear ratio greater than 1:1 so that the shaft and jaws rotate at a faster than the knob when it is turned by a user. The axis of rotation of the knob is offset from the axis of rotation of the shaft so that the knob can project asymmetrically from the body for easier rotation by a user.

9 Claims, 8 Drawing Sheets

ROTATION MECHANISM FOR SURGICAL INSTRUMENTS

CROSS-REFERENCE TO RELATED APPLICATIONS

The present application claims priority to U.S. Provisional No. 62/914,597, filed on Oct. 14, 2019, which is hereby incorporated by reference in its entirety.

BACKGROUND OF THE INVENTION

1. Field of the Invention

The present invention relates to surgical instruments and, more specifically, to a rotation mechanism for easily orienting the jaws of the instrument.

2. Description of the Related Art

Electrosurgical vessel sealers are used for the occlusion of blood vessels and halting of bleeding during surgical procedures. The electrodes of the vessel sealer are carried by a pair of opposing jaws and interconnected to an electrosurgical generator that can selectively supply radiofrequency (RF) energy to the electrodes. A user may close the jaws around a vessel to be sealed by squeezing a lever associated with a handle assembly. The vessel may then be sealed by supplying the RF energy to the clamped vessel. Many instruments include a knob that allows the user to rotate the shaft of the vessel sealer that carries the jaws to more suitably position the jaws around the vessel to be sealed. Conventional knobs, however, are coupled directly to and concentrically with the shaft that supports the jaws. As a result, rotation of the knob results in the shaft rotating through the same number of degrees as the knob, which can make it difficult to position the jaws properly and hard to grasp the know. Accordingly, there is a need in the art for a rotation mechanism that has a knob that is easy to access and that rotates at a different rate than the shaft to which the knob is coupled.

BRIEF SUMMARY OF THE INVENTION

The present invention is an electrosurgical instrument having a rotation knob that is offset from the shaft and interconnected thereto via a set of gears so that the shaft rotates faster than the knob when a user manually rotates the know. The instrument comprises a body supporting a knob having an internal gear, a shaft extending from the body and having an external gear that is coupled to the internal gear of the knob so that the shaft will rotate in response to rotation of the knob, and a pair of jaws mounted to the shaft for rotation therewith in response to rotation of the knob. The shaft is supported within the body for rotation about a first axis. The knob is supported within the body for rotation about a second axis that is offset from the first axis. The internal gear and the external gear have a gear ratio greater than 1:1. A bracket is positioned with the body and coupled to the knob and the shaft. The bracket is coupled the knob by a first set of shoulders that engage a pair of flanges extending from opposite side of the knob. The bracket is coupled the shaft by a second set of shoulders that engage a post positioned at the end of the shaft. The external gear comprises a set of gear teeth extending outwardly from the post. The knob extends asymmetrically from the body.

The present invention also comprises a method of orienting a set of jaws of an electrosurgical instrument. The method includes the step of providing a vessel sealer having body supporting a knob having an internal gear, a shaft extending from the body and having an external gear that is coupled to the internal gear of the knob so that the shaft will rotate in response to rotation of the knob, and a pair of jaws mounted to the shaft for rotation therewith in response to rotation of the knob. The method further includes rotating the knob to cause rotation of the jaws until the jaws are in a desired orientation. The shaft rotates about a first axis during the step of rotating the knob to cause rotation of the jaws until the jaws are in a desired orientation. The knob rotates about a second axis that is offset from the first axis during the step of rotating the knob to cause rotation of the jaws until the jaws are in a desired orientation. The internal gear and the external gear have a gear ratio greater than 1:1 such that the shaft rotates faster than the knob during the step of rotating the knob to cause rotation of the jaws until the jaws are in a desired orientation.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
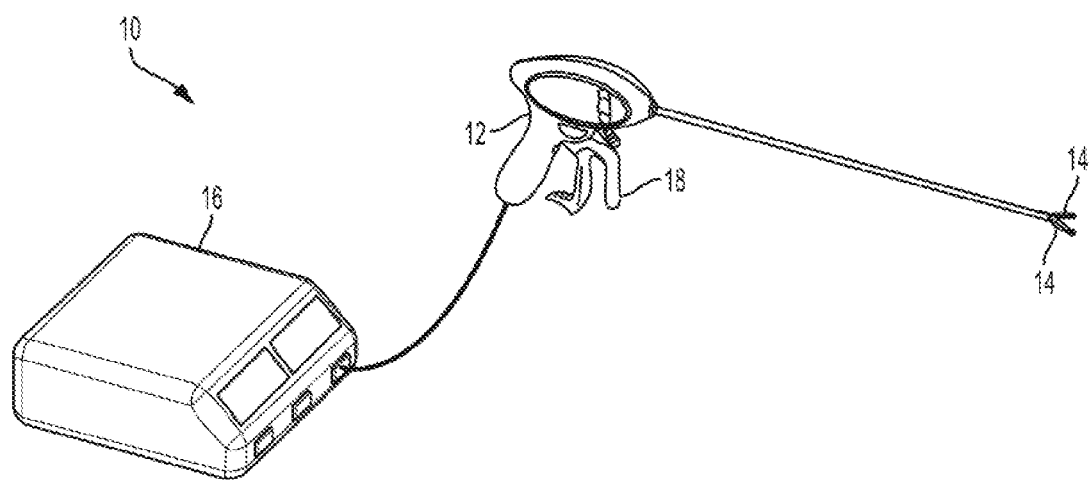
FIG. 1 is a perspective view of an electrosurgical system according to the present invention.

Referring to the figures, wherein like numeral refer to like parts throughout, there is seen in FIG. 1 a vessel sealing system 10 comprising a vessel sealer 12 having a pair of conductive opposing jaws 14 that are interconnected to an electrosurgical generator 16 that can supply RF energy to electrodes of jaws 14 for the desiccation of a blood vessel trapped between jaw 14. The dimensions of jaws 14 and the type of RF energy supplied will produce desiccation of the blood vessel in a region of a particular width as determined by the thermal spread of the energy being supplied to the blood vessel. As is known in the art, jaws 14 are pivotally mounted to vessel sealer 12 for movement between an open position and a closed position in response to a user operating a lever 18 extending from the main body 20 of sealer 12.

Figure 2:
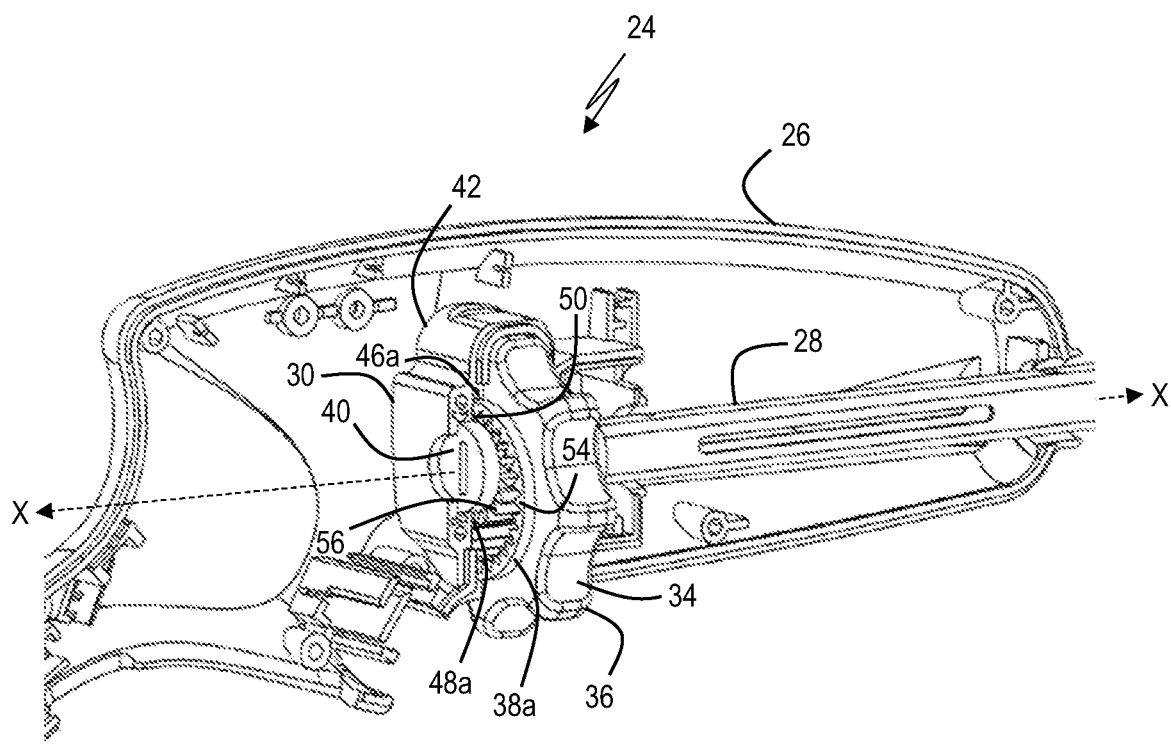
FIG. 2 is a perspective view of the interior of a housing of an electrosurgical device according to the present invention.
Figure 3:
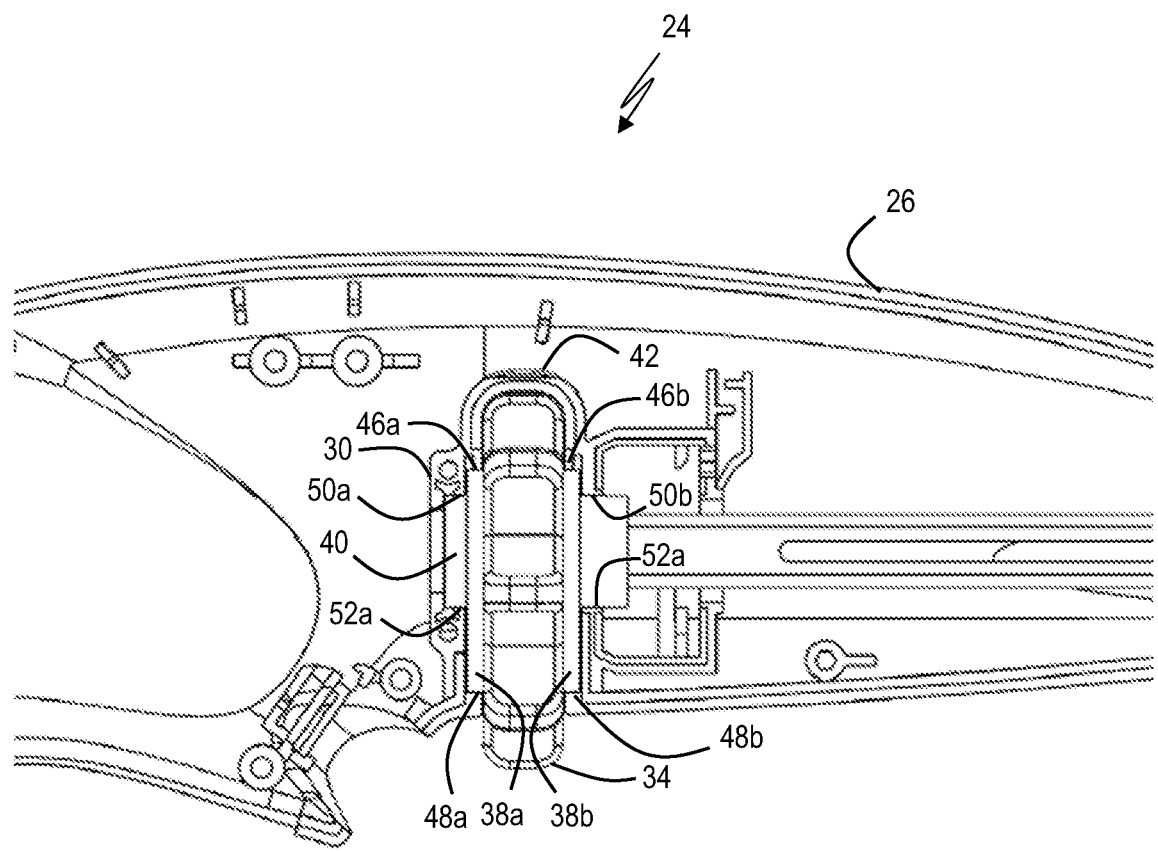
FIG. 3 is a front view of the interior of a housing of an electrosurgical device according to the present invention.

Referring to FIGS. 2 and 3, vessel sealer 12 includes a handle assembly 24 having a body 26. Body 26 is generally formed as two body halves that are coupled together after assembly of the internal components of sealer 12, as is known in the art. Body 26 supports shaft 28 that extends outwardly from body 26. Jaws 14 are mounted to the end of shaft 28 for rotation therewith. Rotation of shaft 28 causes rotation of jaws 14 for proper orientation about a vessel to be sealed. As is known in the art, shaft 28 may encloses a drive member that is coupled to jaws 14 so that longitudinal movement of the drive shaft will mechanically move jaws 14 between the open and closed positioned. Shaft 28 may also include a knife blade that can be extended between the jaws to sever a vessel held between the jaws.

Figure 4:
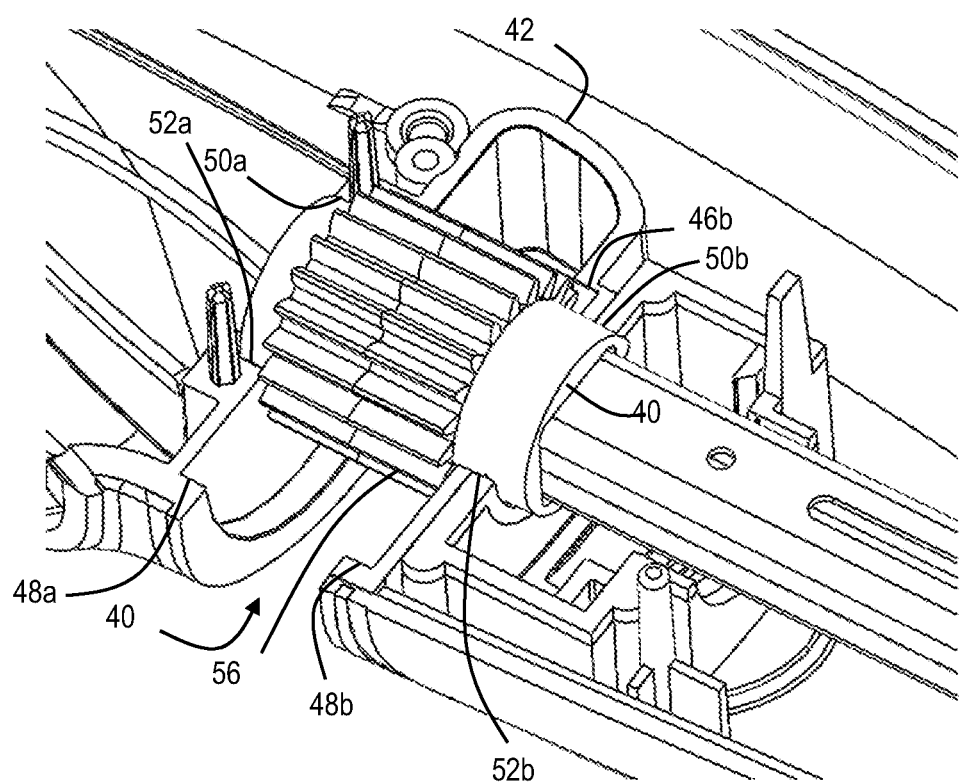
FIG. 4 is a perspective view of the interior of a partially disassembled housing of an electrosurgical device according to the present invention.
Figure 5:
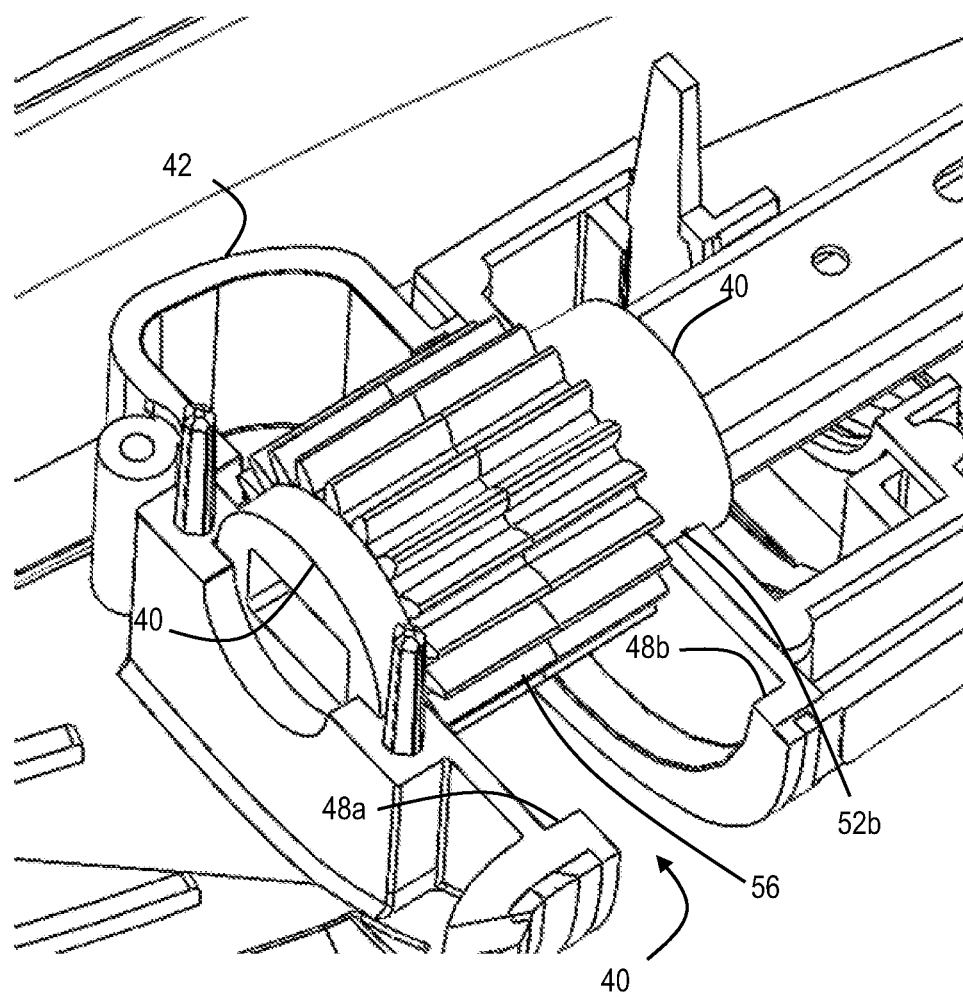
FIG. 5 is a perspective view of the interior of a partially disassembled housing of an electrosurgical device according to the present invention

As seen in FIGS. 3 through 5, body 26 includes a bracket 30 formed therein that supports a knob 34 that is interconnected to shaft 28 so that a user can rotate shaft 28 by rotating knob 34. Bracket 30 supports shaft 28 and knob 34 within body 26 and allows for rotation of both shaft 28 and knob 34. The outer circumference of knob 34 includes a series of grips 36 for easy grasping by a user. Knob 34 further includes a pair of flanges 38a and 38b that extend axially outward to define a pair of circumferentially extending bearing surfaces on either side of knob 34. Bracket 30 extends transversely relative to axis X-X of body 26 and includes an upper portion 42 that extends over knob 34 to partially enclose knob 34 and provide an opening 44 into which knob 34 may be positioned with a portion of knob 34 projecting outwardly from body 26. The inside of bracket 30 includes a first set of shoulders 46a and 46b positioned in abutting relation to flange 38 of knob 34 that cooperate with a second set of shoulders 48a and 48b formed into the interior of housing body 26 to secure knob 34 in body 26 while allowing for rotation of knob 34 via movement of the circumferentially extending bearing surfaces of flanges 38a and 38b against shoulders 46a and 46b and shoulder 48a and 48b. Shaft 28 terminates in a post 40 that extends through knob 34 and is supported by bracket 30 by a third set of shoulders 50a and 50b that cooperate with a fourth set of shoulders 52a and 52b. Shoulders 50a and 50 and shoulders 52a and 52b retain post 40 in place while allowing for rotation of post 40, and thus shaft 28, about axis X-X. Bracket 30 thus supports shaft 28 and knob 34 within body 26 and allows for rotation of both shaft 28 and knob 34.

Figure 6:
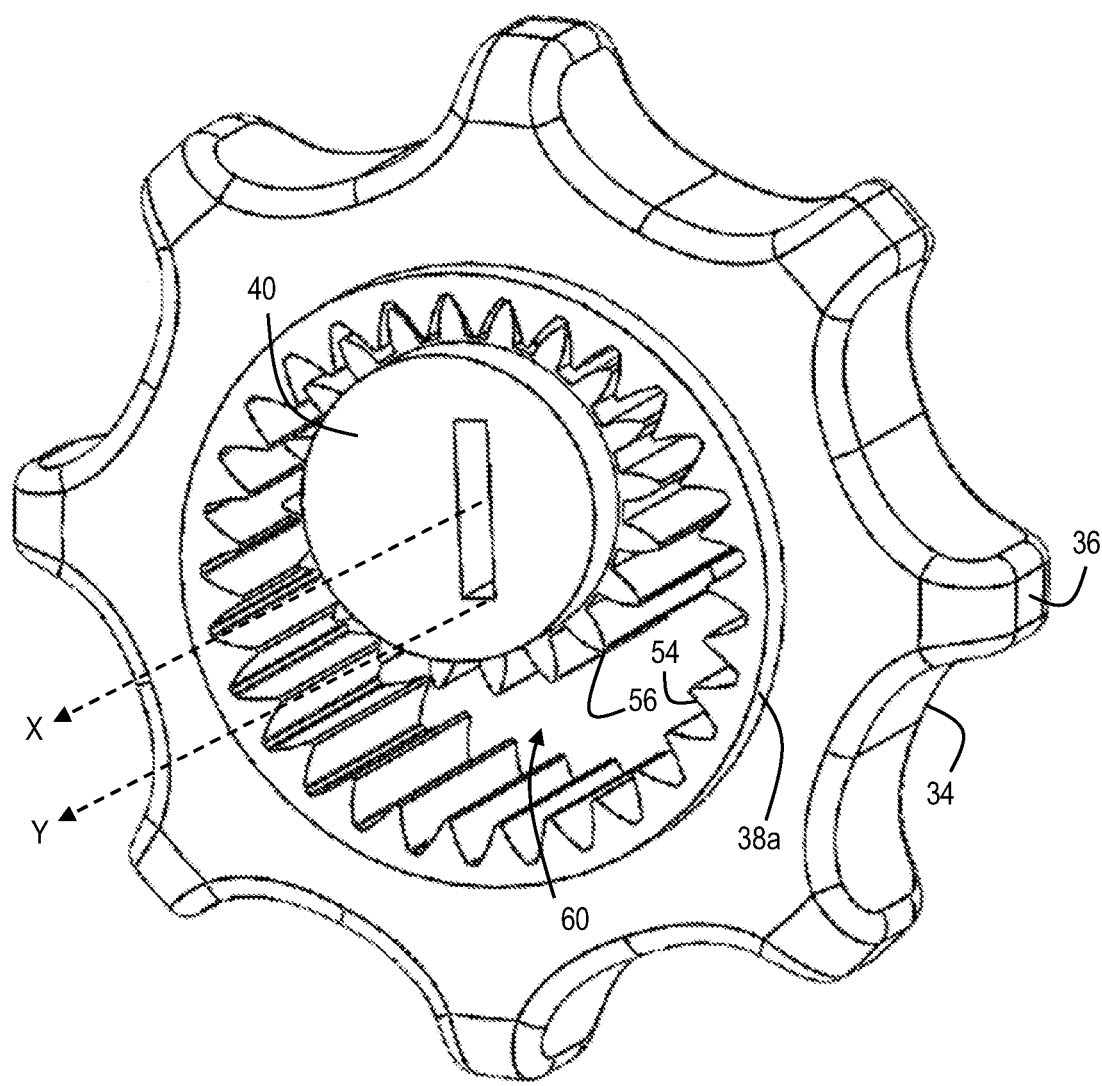
FIG. 6 is a perspective view of a knob gear coupled to a shaft gear according to the present invention.
Figure 7:
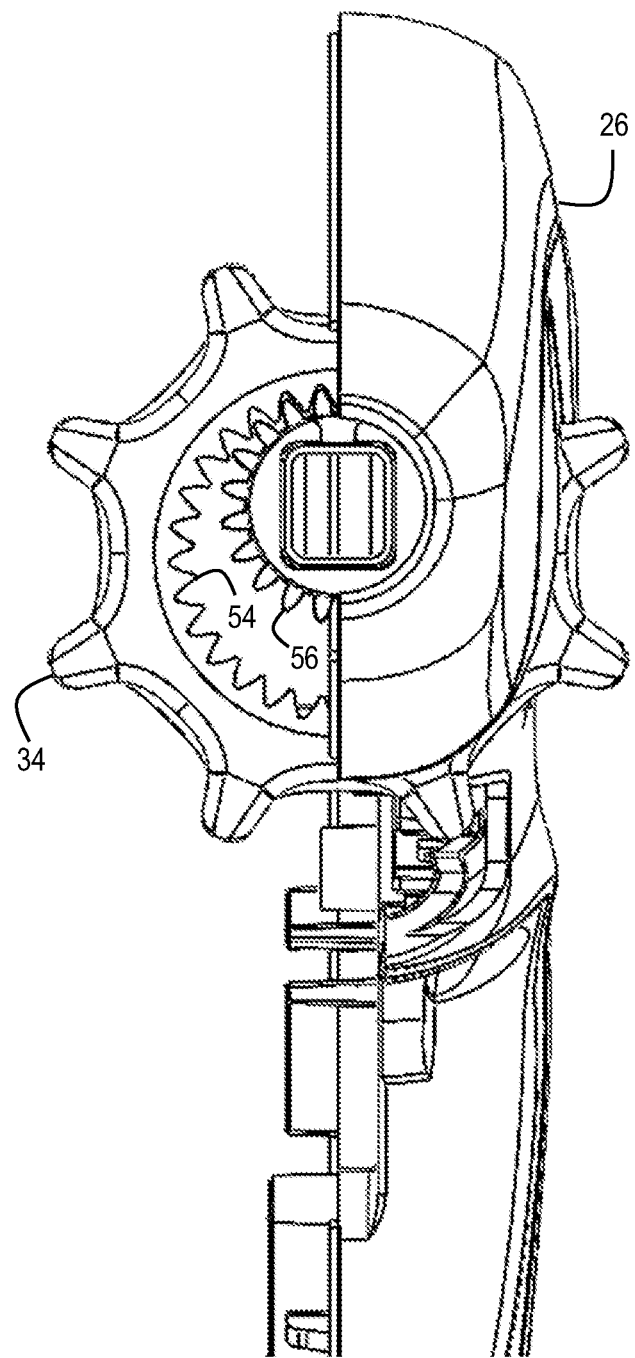
FIG. 7 is a front view of a partially disassembled housing of an electrosurgical device according to the present invention.
Figure 8:
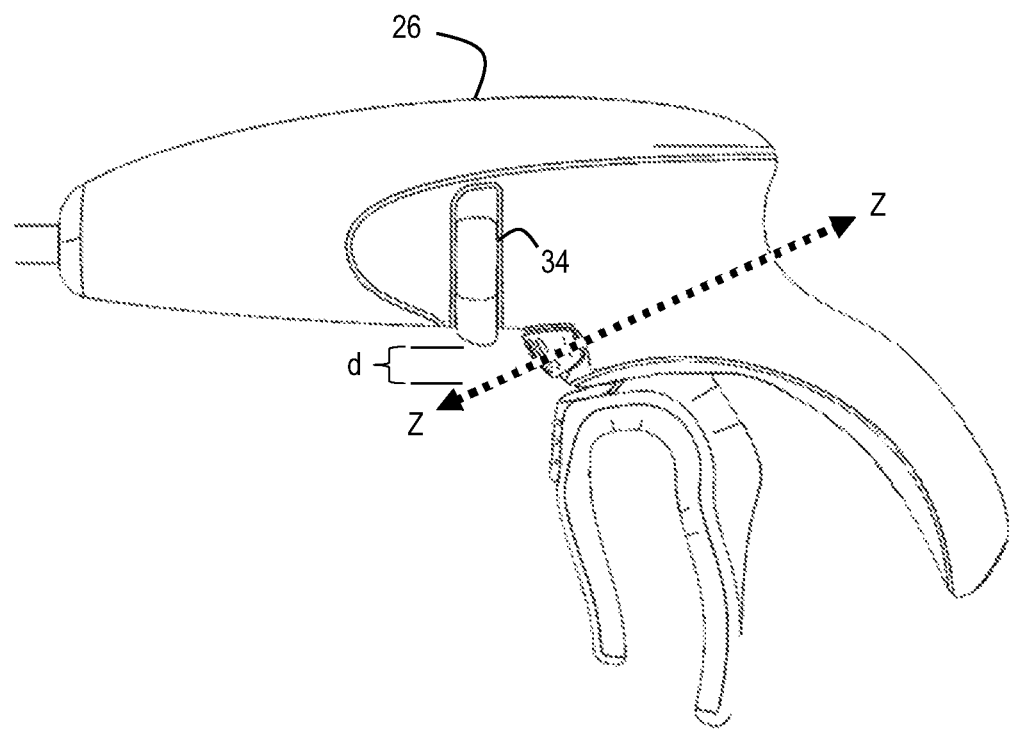
FIG. 8 is a rear view of a housing of an electrosurgical device showing an offset knob according to the present invention.

As seen in FIGS. 2 and 7, knob 34 further comprises a set of gear teeth 54 that extend inwardly toward a central passage 60 to provide an internal gear. Post 40 of shaft 28 passes through passage 60 and is positioned so that the set of gear teeth 54 of knob 34 engage a set of gear teeth 56 that extend outwardly from the outer circumference of post 40 to act as a shaft gear. Gear teeth 54 and gear teeth 56 have similar dimensions and pitch so that shaft 28 will rotate faster than knob 34 as the difference between the inner diameter of the internal gear formed by knob 34 and the external gear formed by post 40 result in a gear ratio that is greater than 1:1. The specific gear ratio may be varied as known in the art to provide any desired gear ratio that is greater than 1:1. For example, a ratio of 1.45 to 1 has been found to be helpful. In addition, as seen in FIG. 6, the axis of rotation of post 40 is aligned along the longitudinal axis X-X of shaft 28 and the axis Y-Y of rotation of knob 34 is offset from axis X-X by to allow the smaller shaft gear and the larger knob gear to intermesh. As an example, an offset of 0.14 inches may be used. As seen in FIG. 7, axis Y-Y may be offset vertically relative to body 26 when held by a user so that knob 34 extends symmetrically on either side of body 26. The vertical offset has the additional advantage of making knob 34 more accessible for a user by positioning the knob closer to the hand of user when using vessel sealer 12. As seen in FIG. 8, line Z-Z representing the alignment of an index finger of a user is spaced distance d from the lower edge of knob 26. Offsetting of knob 34 as describe herein, positioned knob 34 closer to line Z-Z than in conventional designs, thereby making it easier for a user to operate knob 34 with a finger positioned along line Z-Z.

What is claimed is:

1. An electrosurgical instrument, comprising:
    a body having a bracket therein, wherein the bracket includes a first set of shoulders spaced apart from a second set of shoulders;
    a knob having an internal gear and a first axis of rotation about which the knob is free to rotate supported in the body by a first flange extending from the knob and abutting the first set of shoulders and a second flange extending from an opposing side of the know and abutting the second set of shoulders for rotation of the knob within the bracket;
    a shaft extending from the body along a second axis and having an external gear that is coupled directly to the internal gear of the knob so that the shaft will rotate about the second axis in response to rotation of the knob about the first axis, wherein the shaft includes a post positioned at one end and supported in the body by a third set of shoulders of the bracket for rotation of the post within the bracket; and
    a pair of jaws mounted to the shaft for rotation therewith in response to rotation of the knob.

2. The electrosurgical instrument of claim 1, wherein the second axis is offset from the first axis.

3. The electrosurgical instrument of claim 2, wherein the internal gear and the external gear have a gear ratio greater than 1:1.

4. The electrosurgical instrument of claim 1, wherein the external gear comprises a set of gear teeth extending outwardly from the post.

5. The electrosurgical instrument of claim 4, wherein the knob extends asymmetrically from the body.

6. A method of orienting a set of jaws of an electrosurgical instrument, comprising:
    providing a vessel sealer having body supporting a knob having an internal gear and a first axis of rotation about which the knob is free to rotate, wherein the body includes a bracket having a first set of shoulders engaging a first flange extending from the knob and a second set of shoulders engaging a second flange extending from an opposing side of the knob, a shaft extending from the body along a second axis and having an external gear that is directly coupled to the internal gear of the knob so that the shaft will rotate about the second axis in response to rotation of the knob about the first axis, wherein the shaft includes a post positioned at one end that is supported by a third set of shoulders of the bracket for rotation of the post within the bracket, and a pair of jaws mounted to the shaft for rotation therewith in response to rotation of the knob; and
    rotating the knob to cause rotation of the jaws until the jaws are in a desired orientation.

7. The method of claim 6, wherein the second axis is offset from the first axis.

8. The method of claim 6, wherein the external gear comprises a set of gear teeth extending outwardly from the post.

9. The method of claim 8, wherein the knob extends asymmetrically from the body.

\* \* \* \* \*

UNITED STATES PATENT AND TRADEMARK OFFICE
CERTIFICATE OF CORRECTION

PATENT NO. : 12,357,373 B2
APPLICATION NO. : 17/068940
DATED : July 15, 2025
INVENTOR(S) : Aaron Szabo Page 1 of 1

It is certified that error appears in the above-identified patent and that said Letters Patent is hereby corrected as shown below:

In the Claims

In Claim 1 at Column 4, Line 19, the word 'know' should read --knob--

Signed and Sealed this
Twelfth Day of August, 2025

Coke Morgan Stewart
*Acting Director of the United States Patent and Trademark Office*